United States Patent [19]

Sobieray

[11] Patent Number: 6,121,306

[45] Date of Patent: Sep. 19, 2000

[54] METHOD OF MAKING (1S, 4R)-1-AZABICYCLO[2.2.1]HEPTAN-3-ONE AND (1R, 4S), 1-AZABICYCLO[2.2.1]HEPTAN-3-ONE

[75] Inventor: Denis Martin Sobieray, Holland, Mich.

[73] Assignee: Warner-Lambert Company, Morris Plains, N.J.

[21] Appl. No.: 09/355,225

[22] PCT Filed: Jan. 27, 1998

[86] PCT No.: PCT/US98/01413

§ 371 Date: Sep. 29, 1999

§ 102(e) Date: Sep. 29, 1999

[87] PCT Pub. No.: WO98/32759

PCT Pub. Date: Jul. 30, 1998

Related U.S. Application Data

[60] Provisional application No. 60/036,285, Jan. 27, 1997.

[51] Int. Cl.[7] ............ A61K 31/192; A61K 31/194; A61K 31/4015; C07D 209/52
[52] U.S. Cl. ............ 514/413; 514/421; 514/568; 514/574; 548/452; 548/512
[58] Field of Search ................ 548/512, 452; 514/413, 421, 568, 574

[56] References Cited

U.S. PATENT DOCUMENTS 5,346,911  9/1994  Augelli-Szafran et al. ............ 514/339

OTHER PUBLICATIONS

Boelsterli et al., "39. Absolute Configuration of 3–Substituted 1–Azabicyclo[2.2.1]heptanes," Helvetica Chimica Acta, vol. 75, pp. 507–512, 1992.

Jerry March, Advanced Organic Chemistry, Fourth Edition, p. 108, 1992.

*Primary Examiner*—Joseph McKane
*Assistant Examiner*—Jane Osnowski
*Attorney, Agent, or Firm*—Merchant & Gould P.C.

[57] ABSTRACT

Racemic (±)-1-azobicyclo[2.2.1]heptan-3-one may be efficiently resolved into its (1S,4R)- and (1R,4S)-1-azabicyclo[2.2.1]heptan-3-one isomers by formation of di-p-toluoyl hemitartrate salts by combination with di-p-toluoyl-L-tartaric acid and di-p-toluoyl-D-tartaric acid, respectively. Selective crystallization using one of the di-p-toluoyltartaric acids in less than stoichiometric amount in a suitable solvent mixture allows isolation of the desired isomer as its respective di-p-toluoyl hemitartrate in high isomeric purity. The isolated hemitartrates are storage stable and may be used as such in the preparation of pharmaceuticals and other biologically active compounds, or may be used to provide the free base of the respective 1-azabicyclo[2.2.1]heptan-3-one isomer.

19 Claims, No Drawings

METHOD OF MAKING (1S, 4R)-1-AZABICYCLO[2.2.1]HEPTAN-3-ONE AND (1R, 4S), 1-AZABICYCLO[2.2.1]HEPTAN-3-ONE

This application is a 371 of PCT/US98/01413 filed Jan. 27, 1998, and is based on provisional application No. 60/036,285 filed Jan. 27, 1997.

TECHNICAL FIELD

This invention relates to a method of obtaining (1S,4R)-1-azabicyclo[2.2.1]heptan-3-one, the di-p-toluoyl-L-tartaric acid hemisalt of (1S,4R)-1-azabicyclo[2.2.1]heptan-3-one, (1R,4S)-1-azabicyclo[2.2.1]heptan-3-one and the di-p-toluoyl-D-tartaric acid hemisalt of (1R,4S)-1-azabicyclo[2.2.1]heptan-3-one from (±)-1-azabicyclo[2.2.1]heptan-3-one.

BACKGROUND OF THE INVENTION (±)-1-Azabicyclo[2.2.1]heptan-3-one as well as enantiomerically pure forms of 1-azabicyclo[2.2.1]heptan-3-one and mixtures thereof have been shown to be useful in the preparation of compounds which are useful as pharmaceutical agents. See, e.g., U.S. Pat. No. 5,514,812, incorporated herein by reference. Certain compounds formed from enantiomerically pure forms of 1-azabicyclo[2.2.1]heptan-3-one are muscarinic agonists, rendering them useful as pharmaceutical agents in the area of cognition disorders, as disclosed, for example, in U.S. Pat. No. 5,346,911; European Published Applications EP 414,394 A2; EP 427,390 A2; EP 402,056 A2; EP 307,142 A1; and various publications, e.g. H. Tecle et al., BIOORGANIC AND MEDICINAL CHEMISTRY LETTERS, 5, 631–636, (1995) ; H. Tecle, et al., BIOORGANIC AND MEDICINAL CHEMISTRY LETTERS, 5, 637–642, (1995), all incorporated herein by reference.

In order to be commercially viable, an efficient and cost-effective, large scale process for preparing substantially enantiomerically pure forms of 1-azabicyclo[2.2.1]heptan-3-one isomers is needed. Jakob Boelsterli et al., HELV. CHIM. ACTA, 75, 507–12 (1992) prepared (1S,4R)-1-azabicyclo[2.2.1]heptan-3-one by oxidation of (1S,3S,4R)-1-azabicyclo[2.2.1]heptan-3-ol. See also, U.S. Pat. No. 5,346,911. This route involves the formation of racemic 1-azabicyclo[2.2.1]heptan-3-exo-ol in four or more steps. The racemic alcohol is then resolved using D-tartaric acid (unnatural tartaric acid) by formation of a 1 to 1 salt. (1S,3S,4R)-1-azabicyclo[2.2.1]heptan-3-ol is then freed from the D-tartaric acid and recrystallized several times. The (1S,3S,4R)-1-azabicyclo[2.2.1]heptan-3-ol is then oxidized (Swern oxidation) at low temperatures (−60° C.) to give (1S,4R)-1-azabicyclo[2.2.1]heptan-3-one. The crude (1S,4R)-1-azabicyclo[2.2.1]heptan-3-one is then isolated as the hydrochloride salt and recrystallized. A similar reaction sequence is carried out using L-tartaric acid in order to obtain (1R,4S)-1-azabicyclo[2.2.1]heptan-3-one.

Although the route disclosed by the prior art provides (1S,4R)- and (1R,4S)-azabicyclo[2.2.1]heptan-3-ones as the respective hydrochloride salts in high enantiomeric purity, the process is difficult to conduct on large-scale for the following reasons: 1) the process is long, involving at least five steps in addition to the resolution and free alcohol formation steps, 2) the process utilizes a low temperature oxidation step (−60° C.) which requires specialized equipment on a manufacturing scale, and 3) the process relies upon a potentially hazardous oxidation step. In the latter respect, see, e.g., L. Bretherick, "Bretherick's Handbook of Reactive Chemical Hazards", Fourth Edition, Butterworths, Boston, Mass., pp. 299–300 (1990). The known potential alternative to the hazardous oxidation step, utilized in the formation of racemic 1-azabicyclo[2.2.1]heptan-3-one as reported by Spry et al., J. ORG. CHEM, 34, 3674 (1969), does not work as well, and utilizes chromic acid, a toxic and environmentally problematic substance and a known carcinogen. See, e.g., Budavari, S., Ed., THE MERCK INDEX, Twelfth Edition, p. 375, Merck, Whitehouse Station, N.J. (1996). It would be desirable to provide an efficient and economical process for obtaining substantially enantiomerically pure (1S,4R)-1-azabicyclo[2.2.1]heptan-3-one and (1R,4S)-1-azabicyclo[2.2.1]heptan-3-one. It would be further desirable to provide these substantially enantiomerically pure isomers in a stable, easily stored form.

SUMMARY OF THE INVENTION

The present invention provides an efficient means for obtaining (1S,4R)-1-azabicyclo[2.2.1]heptan-3-one, the stable easily stored di-p-toluoyl-L-tartaric acid hemisalt of (1S,4R)-1-azabicyclo[2.2.1]heptan-3-one, (1R,4S)-1-azabicyclo[2.2.1]heptan-3-one, and the stable easily stored di-p-toluoyl-D-tartaric acid hemisalt of (1R,4S)-1-azabicyclo[2.2.1]heptan-3-one. It is readily conducted on a scale suitable for commercial use and involves at least 2 fewer steps than the published procedure. It further avoids the use of low temperature reactions, the use of a potentially hazardous oxidation step, and the use of toxic chromic acid. Unexpectedly, the resolution procedure of the present invention provides a salt in which both of the carboxylic acid groups of the respective resolving agents, di-p-toluoyl-L-tartaric acid or di-p-toluoyl-D-tartaric acid, are efficiently utilized in the formation of a 2 to 1 salt (hemisalt). Therefore, the process may be carried out using less resolving agent than expected, resulting in a more economical process. In addition, the resolution procedure was unexpectedly found to give a stable, easily stored salt which can be converted to compounds of pharmaceutical interest without the need for prior isolation of the 1-azabicyclo[2.2.1]heptan-3-one free base. The process comprises combining (±)-1-azabicyclo[2.2.1]heptan-3-one and di-p-toluoyl-L-tartaric acid in an appropriate solvent or solvent mixture, allowing a precipitate to form, and collecting the solid precipitated (1S,4R)-1-azabicyclo[2.2.1]heptan-3-one hemisalt; or combining (±)-1-azabicyclo[2.2.1]heptan-3-one and di-p-toluoyl-D-tartaric acid in an appropriate solvent or solvent mixture, allowing a precipitate to form, and recovering the precipitated (1R,4S)-1-azabicyclo[2.2.1]heptan-3-one hemisalt. The respective hemisalts (hemitartrates) may be stored as the hemisalt, or may be reacted with base to liberate the respective 1-azabicyclo[2.2.1]heptan-3-one free base.

DESCRIPTION OF THE PREFERRED EMBODIMENTS

The present invention provides the compounds:

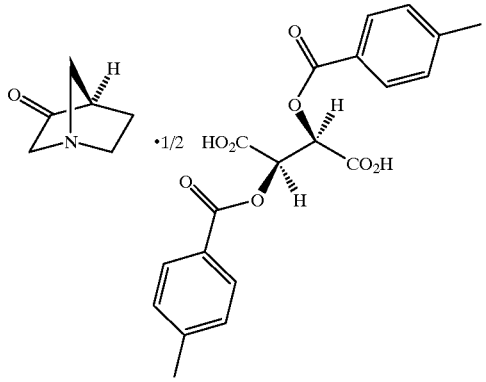

and

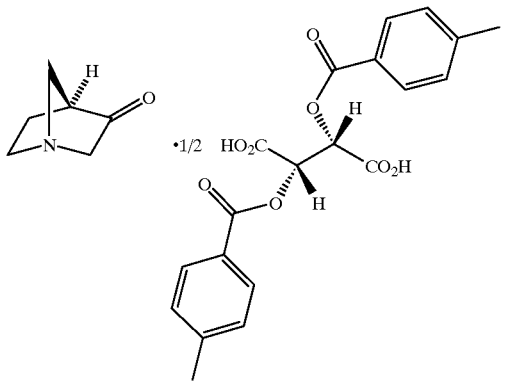

and a process for their preparation. (±)-1-azabicyclo[2.2.1]heptan-3-one may be prepared by known methods. See, e.g., Saunders et al., J. CHEM. SOC., CHEM. COMMUN., 24, 1618–9 (1988); Street et al., J. MED. CHEM. 33 2690–7 (1990); European Published Patent Application EP 307,140 A1; European Published Patent Application EP 414,394 A2; U.S. Pat. Nos. 5,217,975 and 5,405,853; and European Published Patent Application EP 239,309 A2. (1S,4R)-1-Azabicyclo[2.2.1]heptan-3-one may be obtained from (±)-1-azabicyclo[2.2.1]heptan-3-one by combining racemic (±)-1-azabicyclo[2.2.1]heptan-3-one and di-p-toluoyl-L-tartaric acid in a protic or aprotic solvent or a mixture of protic or aprotic solvents; allowing a precipitate to form; and collecting the solid precipitate. The (1R,4S) isomer, (1R,4S)-1-azabicyclo[2.2.1]heptan-3-one may be obtained from (±)-1-azabicyclo[2.2.1]heptan-3-one by combining (±)-1-azabicyclo[2.2.1]heptan-3-one and di-p-toluoyl-D-tartaric acid in a similar solvent or solvent mixture; allowing a precipitate to form; and collecting the solid precipitate. The reaction sequence for preparation of (1S,4R)-1-azabicyclo[2.2.1]heptan-3-one, di-p-toluoyl-L-tartaric acid hemisalt and the corresponding free base, (1S,4R)-1-azabicyclo[2.2.1]heptan-3-one, is illustrated in accordance with Scheme I below:

Scheme I

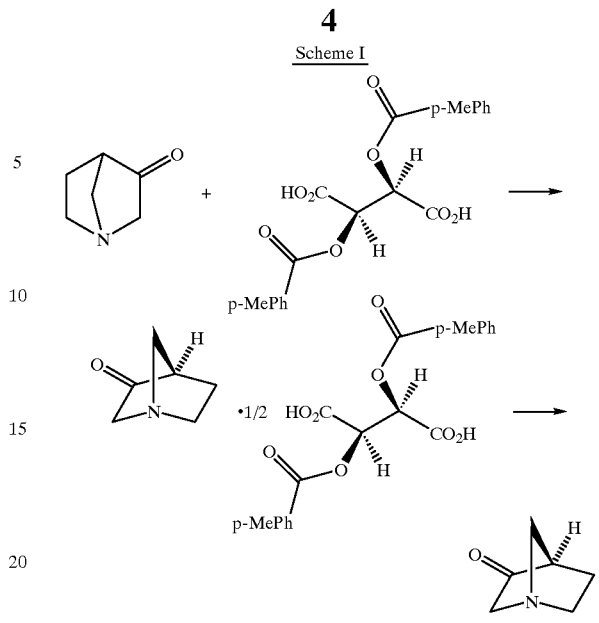

Scheme I

Scheme I illustrates a method for obtaining the di-p-toluoyl-L-tartaric acid hemisalt of (1S,4R)-1-azabicyclo[2.2.1]heptan-3-one from (±)-1-azabicyclo[2.2.1]heptan-3-one and for obtaining (1S,4R)-1-azabicyclo[2.2.1]heptan-3-one from (±)-1-azabicyclo[2.2.1]heptan-3-one, the method comprising combining (±)-1-azabicyclo[2.2.1]heptan-3-one and di-p-toluoyl-L-tartaric acid in a protic or aprotic solvent or a mixture of protic or aprotic solvents; allowing a precipitate to form; and collecting the solid precipitate corresponding to the di-p-toluoyl-L-tartaric acid hemisalt, and obtaining the free base by treatment with base. Scheme II reflects the identical reaction sequence employing di-p-toluoyl-D-tartaric acid, whereby the di-p-toluoyl-D-tartaric acid hemisalt of (1R,4S)-1-azabicyclo[2.2.1]heptan-3-one precipitates, from which the free base (1R,4S)-1-azabicyclo[2.2.1]heptan-3-one can be liberated.

Scheme II

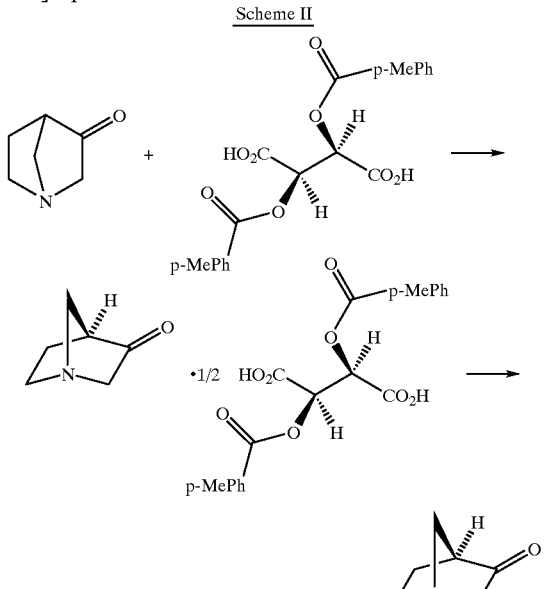

Scheme II (±)-1-Azabicyclo[2.2.1]heptan-3-one can be resolved in accordance with the present invention, i.e. the enantiomers separated, by selective crystallization with di-p-toluoyl-L-tartaric acid or di-p-toluoyl-D-tartaric acid. (±)-1-Azabicyclo[2.2.1]heptan-3-one and either (but not both) di-p-toluoyl-L-tartaric acid or di-p-toluoyl-D-tartaric acid can be combined in solvents such as alcohols, ethers, esters, nitrites, mixtures of water and one or more alcohols, or mixtures of the aforementioned solvents. Examples of suitable alcohols include methanol, ethanol, n-propanol, isopropyl alcohol, n-butanol, tert-butanol, and the like. Examples of suitable ethers include diethyl ether, tert-butylmethyl ether, tetrahydrofuran and the like. Examples of suitable esters include methyl acetate, ethyl acetate, isopropyl acetate, n-butyl acetate and the like. Examples of suitable nitrites include acetonitrile and the like. This list of solvents is illustrative and not limiting.

The suitability of a given solvent mixture may be readily assessed by adding (±)-1-azabicyclo[2.2.1]heptan-3-one and the particular di-p-toluoyltartaric acid to the solvent mixture in the presence of seed crystals of the respective hemitartrate salt. The precipitate can be collected and its quantity gravimetrically determined. Its purity can be assessed by HPLC using a chiral adsorbent. Such determinations are easily performed by one skilled in the art. A solvent or solvent mixture which provides the desired purity, generally greater than 90% pure with respect to the 1-azabicyclo[2.2.1]heptan-3-one isomers, and in sufficient quantity (i.e. solubility is not too great), is a "selective crystallization-effective" solvent or solvent mixture as that term is used herein.

In general, the (1S,4R) isomer of 1-azabicyclo[2.2.1]heptan-3-one precipitates from the solution as approximately a 2 to 1 salt with di-p-toluoyl-L-tartaric acid. A shortage of di-p-toluoyl-L-tartaric acid is preferably used in order that a product of high isomeric purity is obtained. Additional di-p-toluoyl-L-tartaric acid can be used in the crystallization if a lower isomeric purity can be tolerated in the product. For example, the stoichiometry relative to di-p-toluoyltartaric acid is calculated based on the formation of the hemitartrate of the desired isomer. Thus, 1 mol of racemic (±)-1-azabicyclo[2.2.1]heptan-3-one will contain 0.5 mol of the (1S,4R) isomer, or 0.5 mol-equivalent. Since the hemitartrate is formed in the reaction, 1 mol of di-p-toluoyl-L-tartaric acid represents 2 mol-equivalents. Thus, for 1 mol (±)-1-azabicyclo[2.2.1]heptan-3-one, the stoichiometric amount of di-p-toluoyl-L-tartaric acid required to form the respective hemitartrate is 0.25 mol. However, it is generally desirable to enhance the isomeric purity of the product. Enhanced isomeric purity may be achieved by utilizing from 50% to about 95% of the stoichiometric amount of the respective di-p-toluoyltartaric acid, more preferably from about 70% to 90% of this amount. Thus, to resolve 1 mol of the racemic mixture of (±)-1-azabicyclo [2.2.1]heptan-3-one and isolate a substantially pure (1S,4R)-1-azabicyclo[2.2.1]heptan-3-one di-p-toluoyl-hemi-(L)-tartrate, approximately 0.20 mol of di-p-toluoyl-L-tartaric acid may be used. Similarly, when isolating the (1R,4S) isomer, di-p-toluoyl-D-tartaric acid is employed, the (1R,4S) isomer precipitating as a 2:1 salt (hemisalt; hemitartrate) with the resolving agent.

Removal of the respective di-p-toluoyltartaric acid from the hemitartrate salt to give the respective isomer-enriched 1-azabicyclo[2.2.1]heptan-3-one free base can be accomplished by methods well known to those skilled in the art, or by partitioning the salt between an acidic aqueous phase, such as aqueous hydrochloric acid, and an organic phase, such as tert-butylmethyl ether. The acidic aqueous phase may then be concentrated, and rendered basic by the addition of a base such as potassium carbonate, sodium hydroxide or the like. Extraction of the aqueous phase with an appropriate solvent such as ethyl acetate, methylene chloride, chloroform, or the like followed by removal of the solvent from the organic extracts by distillation gives the enriched (1S,4R)-1-azabicyclo[2.2.1]heptan-3-one.

Following separation of the desired isomer as its respective di-p-toluoyl hemitartrate salt by precipitation from solution, a second, somewhat less pure crop of crystals may be collected by addition of further amounts of the particular di-p-toluoyltartaric acid to the mother liquor and cooling to a temperature sufficient to precipitate further amounts of the hemisalt. In general, this temperature is lower than that of the first precipitation (crystallization). Both precipitations are advantageously promoted through addition of seed crystals of the desired isomerically pure product.

If it is desired to isolate the non-precipitated isomer, a quantity of the requisite di-p-toluoyltartaric acid may be added to the solution and precipitate collected as before. For example, if di-p-toluoyl-L-tartaric acid is added to (±)-1-azabicyclo[2.2.1]heptan-3-one to precipitate the di-p-toluoyl-L-hemitartrate of (1S,4R)-1-azabicyclo[2.2.1] heptan-3-one, this precipitation may be followed by addition of a further amount of di-p-toluoyl-L-tartaric acid to recover a second crop of somewhat less pure (1S,4R)-1-azabicyclo [2.2.1]heptan-3-one. The (1R,4S) isomer enriched 1-azabicyclo[2.2.1]heptan-3-one may then be isolated from the mother liquor by methods well known to those skilled in the art.

It is entirely feasible, and desired, to combine mixtures having enriched concentrations of the desired isomer for further purification. For example, mixtures containing the hemitartrate of (1S,4R)-1-azabicyclo[2.2.1]heptan-3-one in isomeric purities of less than 90% may be combined and recrystallized, or may be converted to the respective free base, and reprecipitated with di-p-toluoyl-L-tartaric acid, to obtain the hemitartrate in high purity, typically greater than 95%. The mother liquor will still contain further (1S,4R)-isomer and can be combined with other similar mother liquor fractions for later purification. In this manner, expensive starting materials are conserved in an economical fashion. The di-p-toluoyl-L-tartaric acid and di-p-toluoyl-D-tartaric acid resolving agents can themselves be separated, i.e. after liberation of the 1-azabicyclo[2.2.1] heptan-3-one free base, and purified by conventional techniques.

It was highly surprising that the use of the (L) and (D) di-p-toluoyltartric acids facilitated such an efficient resolution of the (1S,4R) and (1R,4S) isomers of (±)-1-azabicyclo [2.2.1]heptan-3-one. It was even more surprising that the respective hemitartrates were formed, allowing the resolution of 2 mols of 1-azabicyclo[2.2.1]heptan-3-one for only 1 mol of resolving agent. Not only is the process efficient, but most importantly, it is capable of practice in commercial scale quantities, all without use of low temperature, potentially dangerous oxidation, or use of environmentally questionable and carcinogenic oxidizing agents such as chromium trioxide.

The inventive process allows the isolation of the desired isomers as storage stable salts. Thus, also provided by the present invention are the novel compounds:

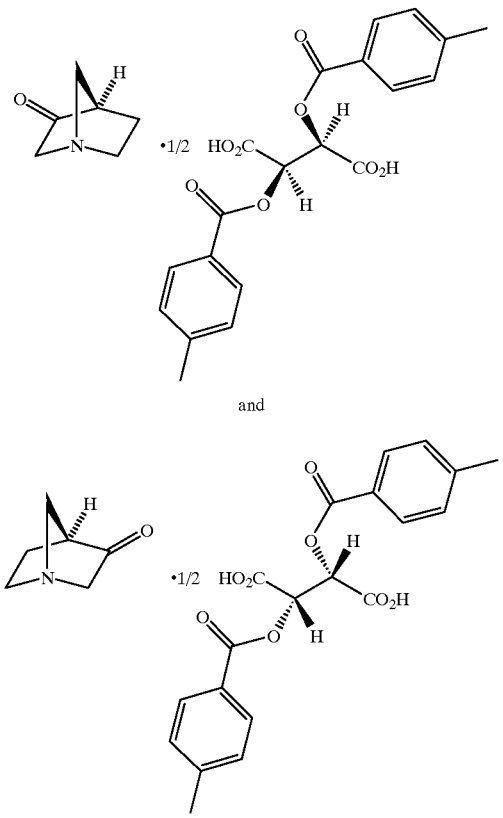

and

It is contemplated that the compounds of the present method can be found or isolated in the form of hydrates or solvates as well as the hemitartrates per se, all of which are considered to fall within the scope of the present invention.

The examples below are intended to illustrate specific embodiments of the invention and are not intended to limit the scope of the specification, including the claims, in any manner.

EXAMPLES

Example 1

Formation of (1S,4R)-1-azabicyclo[2.2.1]heptan-3-one, di-p-toluoyl-L-tartaric acid hemisalt Di-p-toluoyl-L-tartaric acid (20.0 kg, 51.8 mol) was dissolved in acetonitrile (55 kg) and heated to 40–43° C. with agitation. Seed crystals of (1S,4R)-1-azabicyclo[2.2.1] heptan-3-one, di-p-toluoyl-L-tartaric acid hemisalt (0.1 kg) were added. (±)-1-Azabicyclo[2.2.1]heptan-3-one (28.8 kg dissolved in 26.1 kg ethyl acetate, 259 mol) was dissolved in acetonitrile (115 kg) and heated to 40–43° C. The (±)-1-azabicyclo[2.2.1]heptan-3-one solution was added to the di-p-toluoyl-L-tartaric acid solution over a period of 2 hours. The mixture was cooled to 20–25° C. over a period of 1 hour. The solid product was collected by filtration and washed with cold acetonitrile (40 kg). The product was dried under reduced pressure (2 mmHg) at 40–45° C. for 21–22 hours to give 27.0 kg of product. Chiral HPLC: (Chiralpak AD (Chiral Technologies, Inc., Exton, Pa.) Hexane/IPA/DEA, 70:30:0.1, (solution concentration: ~40 mg sample dissolved in ~5 mL isopropyl alcohol containing 5 drops of diethylamine)) enantiomeric purity 97.2% (1S,4R)-1-azabicyclo[2.2.1]heptan-3-one. $^1$H-NMR (DMSO, 200 MHZ): δ 9.6 (s (broad), 1H), 7.87 (d, 2H, J=8.1 Hz), 7.35 (d, 2H, J=8.1 Hz), 5.69 (s, 1H), 3.28–2.99 (m, 4H), 2.92–2.81 (m, 3H), 2.38 (s, 3H), 2.19–2.02 (m, 1H), 1.71–1.58 (m, 1H). $^{13}$C-NMR (DMSO, 50 MHZ): δ 213.2, 168.5, 164.8, 143.8, 129.3, 129.2, 126.7, 72.4, 62.1, 58.0, 50.9, 47.4, 24.2, 21.1. IR (KBr): 700.0, 757.9, 1112.7, 1128.2, 1172.5, 1268.9, 1342.2, 1612.2, 1718.3, 1772.3, 2989.1, 3008.4 cm$^{-1}$.

Additional material may be obtained from the filtrate using the following procedure:

Di-p-toluoyl-L-tartaric acid (7.5 kg, 19 mol) was dissolved in acetonitrile (7.5 kg) at 20–25° C. The di-p-toluoyl-L-tartaric acid solution was added to the acetonitrile filtrate. Seed crystals of (1S,4R)-1-azabicyclo[2.2.1]heptan-3-one, di-p-toluoyl-L-tartaric acid hemisalt (0.05 kg) were added. The mixture was cooled to 0–5° C. and stirred for 1–2 hours. The solid was collected by filtration and washed with cold acetonitrile (20 kg). The solid was dried under reduced pressure (4 mmHg) at 40–45° C. for 19 hours to give 6.1 kg of crude product. Chiral HPLC: 91.1% (1S,4R)-1-azabicyclo[2.2.1]heptan-3-one. The crude product (6.1 kg, 20 mol) was dissolved in methanol (6.1 kg) and added to a mixture of isopropyl alcohol (45 L) and (1S,4R)-1-azabicyclo[2.2.1]heptan-3-one, di-p-toluoyl-L-tartaric acid hemisalt seed crystals (0.04 kg) at 20–25° C. The mixture was stirred at 20–25° C. for 1 hour. The solid was collected by filtration and washed with isopropyl alcohol (15 L). The product was dried under reduced pressure (3 mmHg) at 40–45° C. for 20–21 hours to give 4.6 kg of product. Chiral HPLC: 98.4% (1S,4R)-1-azabicyclo[2.2.1]heptan-3-one.

Example 2

Formation of (1S,4R)-1-azabicyclo[2.2.1]heptan-3-one, di-p-toluoyl-L-tartaric acid hemisalt (±)-1-Azabicyclo[2.2.1]heptan-3-one (15 g, 135 mmol) was dissolved in acetonitrile (60 g). The solution was heated to 40–43° C. Seed crystals of (1S,4R)-1-azabicyclo[2.2.1] heptan-3-one, di-p-toluoyl-L-tartaric acid hemisalt were added. Di-p-toluoyl-L-tartaric acid (10.4 g, 34 mmol) dissolved in acetonitrile (29 g) was added dropwise over a period of 2.25 hours. The mixture was cooled to 25° C. The mixture was filtered and the solid was washed with acetonitrile (30 g, 23° C.). The solid was dried under reduced pressure (60° C.) to give 13.48 grams of product as a white solid. Chiral HPLC: 98.3% (1S,4R)-1-azabicyclo[2.2.1] heptan-3-one.

Example 3

Formation of (1S,4R)-1-azabicyclo[2.2.1]heptan-3-one (1S,4R)-1-azabicyclo[2.2.1]heptan-3-one, di-p-toluoyl-L-tartaric acid hemisalt (14.3 g, 0.047 mol) was placed in tert-butylmethylether (200 g) and extracted with 1 molar aqueous hydrochloric acid solution (130 mL). The aqueous extract was concentrated under reduced pressure at 70° C. Ethyl acetate (30 g) and saturated aqueous potassium carbonate (7 g) were added. The layers were separated and the aqueous layer was extracted with ethyl acetate (20 g). The two ethyl acetate solution were combined and the solvent was removed under reduced pressure at 22° C. to give 3.4 g of (1S,4R)-1-azabicyclo[2.2.1]heptan-3-one. HPLC: (Zorbax 300-SCX (MAC-MOD Analytical, Inc., Chadds Ford, Pa.) 0.03 molar KH$_2$PO$_4$ (adjusted to pH 2.5 with H$_3$PO$_4$)/methanol, 1:1) purity 96%.

Example 4

Formation of (1R,4S)-1-azabicyclo[2.2.1]heptan-3-one, di-p-toluoyl-D-tartaric acid hemisalt (±)-1-Azabicyclo[2.2.1]heptan-3-one (15 g, 135 mmol) is dissolved in acetonitrile (approximately 60 g). The solution is heated to 40–43° C. Seed crystals of (1R,4S)-1-azabicyclo[2.2.1]heptan-3-one, di-p-toluoyl-D-tartaric acid hemisalt are added. Di-p-toluoyl-D-tartaric acid (10.4 g, 34 mmol) dissolved in acetonitrile (approximately 29 g) is added dropwise. The mixture is cooled to 25° C. The mixture is filtered and the solid is washed with acetonitrile. The solid is dried under reduced pressure to give the product as a white solid.

Example 5

Formation of (1R,4S)-1-azabicyclo[2.2.1]heptan-3-one (1S,4R)-1-azabicyclo[2.2.1]heptan-3-one, di-p-toluoyl-L-tartaric acid hemisalt (14.3 g, 0.047 mol) is placed in tert-butylmethylether (approximately 200 g) and extracted with 1 molar aqueous hydrochloric acid solution (approximately 130 mL). The aqueous extract is concentrated under reduced pressure. Ethyl acetate (approximately 30 g) and saturated aqueous potassium carbonate (approximately 7 g) are added. The layers are separated and the aqueous layer is extracted with ethyl acetate (approximately 20 g). The two ethyl acetate solution are combined and the solvent is removed under reduced pressure to give (1R,4S)-1-azabicyclo[2.2.1]heptan-3-one.

Example 6

Formation of (4R)-1-azabicyclo[2.2.1]heptan-3-one, O-[3-(3-methoxyphenyl)-2-propynyl]oxime The utility of the resolved hemitartrate salts is illustrated herein. (1S,4R)-1-azabicyclo[2.2.1]heptan-3-one, di-p-toluoyl-L-tartaric acid hemisalt, (4.57 g) and O-(m-methoxyphenylpropargyl)hydroxylamine oxylate (3.26 g) were dissolved in di-methylsulfoxide (DMSO) (20 mL). Triethylamine (7.0 g) was added at 20° C. After 1 day at room temperature additional O-(m-methoxyphenylpropargyl)hydroxylamine oxylate (0.56 g) and triethylamine (1.2 g) were added. After an additional 6 days at room temperature additional O-(m-methoxyphenylpropargyl)hydroxylamine oxylate (0.76 g) and triethylamine (2 g) were added. After 1 day at room temperature the mixture was heated to 60–70° C. for 1 hours. The mixture was reduced in volume by distillation under reduced pressure until a homogeneous solution with a weight of approximately 35 g was obtained. The mixture was combined with water (10 mL), saturated aqueous sodium bicarbonate solution (30 mL) and tert-butylmethylether (30 mL). The mixture was filtered and the phases were separated. The aqueous phase was extracted with tert-butylmethylether (3×50 mL). The tert-butylmethylether extracts were combined and the solvent was removed under reduced pressure to give (4R)-1-azabicyclo[2.2.1]heptan-3-one, O-[3-(3-methoxyphenyl)-2-propynyl)oxime (4.33 g) as a mixture of E and Z isomers. The oil was dissolved in tert-butylmethylether (25 mL) and extracted with aqueous citric acid (1×20 mL, and 1×10 mL of 0.33 M). The aqueous extracts were combined and the pH was adjusted to 8.5 with sodium bicarbonate. The aqueous mixture was extracted with tert-butylmethylether (2×25 mL). The tert-butylmethylether extracts were combined and extracted with water (10 mL). The organic phase was concentrated under reduced pressure at 40–48° C. to give 3.52 g of (4R)-1-azabicyclo[2.2.1]heptan-3-one, O-[3-(3-methoxyphenyl)-2-propynyl)oxime. HPLC: (Zorbax SB-CN (MAC-MOD Analytical, Inc., Chadds Ford, Pa.) 0.05 molar triethylamine (adjusted to pH 3 with $H_3PO_4$)/acetonitrile/methanol, 8:1:1) purity 98% by area as a 39:61 mixture of E and Z isomers, di-p-toluoyl-L-tartaric acid content <0.05%.

Example 6 illustrates the utility of the respective hemitartrate salts without the necessity of first isolating the free base. The product of Example 6 particularly the Z-isomer, is known to exhibit anti-muscarinic activity.

By the claim term "substantially one but not both" relative to the compound pairings (1S,4R)-1-azabicyclo[2.2.1]heptan-3-one/di-p-toluoyl-L-tartaric acid; and (1R,4S)-1-azabicyclo[2.2.1]heptan-3-one/di-p-toluoyl-D-tartaric acid is meant a separable mixture containing predominately one compound pairing but not the other. The term does not simply mean that the separable mixture is free of the other compound pairing, but that the other compound pairing, if present, is present in such quantity that its concentration will not interfere with obtaining a precipitate which is enriched in the desired di-p-toluoyltartrate hemisalt. The amount of the "non-desired" isomer/di-p-toluoyltartaric acid pairing which is tolerable may also be described as a "non-enrichment interfering amount." The term "substantially enantiomerically pure" and similar terms used herein are as understood by one skilled in the art. Substantial enantiomeric purity is preferably greater than 90% pure relative to the isomers in question, more preferably greater than 95% pure, and most preferably greater than 98% pure on this basis.

Having now fully described the invention, it will be apparent to one of ordinary skill in the art that many changes and modifications can be made thereto without departing from the spirit or scope of the invention as set forth herein.

What is claimed is:

1. A process for the resolution of one desired (1R,4S) or (1S,4R) isomer of (±)-1-azabicyclo[2.2.1]heptan-3-one, said process comprising:

a) dissolving a mixture of (1R,4S)- and (1S,4R)-1-azabicyclo[2.2.1]heptan-3-one in a selective crystallization-effective solvent comprising one or more protic and/or aprotic solvents to form a separable mixture;

b) combining with said separable mixture a di-p-toluoyltartaric acid isomer such that substantially one but not both of the following pairs of compounds will be present in said separable mixture:

b)I) (1S,4R)-1-azabicyclo[2.2.1]heptan-3-one and di-p-toluoyl-L-tartaric acid; or b)ii) (1R,4S)-1-azabicyclo[2.2.1]heptan-3-one and di-p-toluoyl-d-tartaric acid;

c) allowing a precipitate to form and collecting said solid precipitate from the mother liquid of said separable mixture, said precipitate comprising:

c)I) (1S,4R)-1-azabicyclo[2.2.1]heptan-3-one, di-p-toluoyl-L-tartaric acid hemisalt; or c)ii) (1R,4S)-1-azabicyclo[2.2.1]heptan-3-one, di-p-toluoyl-D-tartaric acid hemisalt;

wherein a precipitate comprising c)I) is obtained when said separable mixture comprises b)I) and wherein a precipitate comprising c)ii) is obtained when said separable mixture comprises b)ii).

2. The process of claim 1 wherein said one desired isomer is (1S,4R)-1-azabicyclo[2.2.1]heptan-3-one, said di-p-toluoyltartaric acid is di-p-toluoyl-L-tartaric acid, and said precipitate comprises (1S,4R)-1-azabicyclo[2.2.1]heptan-3-one, di-p-toluoyl-L-tartaric acid hemisalt.

3. The process of claim 1 wherein said one desired isomer is (1R,4S)-1-azabicyclo[2.2.1]heptan-3-one, said di-p-toluoyltartaric acid is di-p-toluoyl-D-tartaric acid, and said precipitate comprises (1R,4S)-1-azabicyclo[2.2.1]heptan-3-one, di-p-toluoyl-D-tartaric acid hemisalt.

4. The process of claim 2 wherein said di-p-toluoyl-L-tartaric acid is combined with said separable mixture in an amount of from about 50% to about 100% of stoichiometry calculated as the hemisalt from the amount of (1S,4R) isomer contained in said separable mixture.

5. The process of claim 2 wherein said di-p-toluoyl-L-tartaric acid is combined with said separable mixture in an amount of from about 70% to about 90% of stoichiometry calculated as the hemisalt from the amount of (1S,4R) isomer contained in said separable mixture.

6. The process of claim 3 wherein said di-p-toluoyl-D-tartaric acid is combined with said separable mixture in an amount of from about 50% to about 100% of stoichiometry calculated as the hemisalt from the amount of (1R,4S) isomer contained in said separable mixture.

7. The process of claim 3 wherein said di-p-toluoyl-D-tartaric acid is combined with said separable mixture in an amount of from about 70% to about 90% of stoichiometry calculated as the hemisalt from the amount of (1R,4S) isomer contained in said separable mixture.

8. The process of claim 1 wherein said selective crystallization solvent comprises one or more of alcohol solvents, ether solvents, ester solvents, and nitrile solvents.

9. The process of claim 1 wherein said selective crystallization solvent is selected from the group consisting of acetonitrile, ethyl acetate and isopropyl alcohol.

10. A process for the resolution of (1S,4R)-1-azabicyclo[2.2.1]heptan-3-one, said process comprising:
 a) dissolving a mixture of (1R,4S)- and (1S,4R)-a-azabicyclo[2.2.1]heptan-3-one in a selective crystallization—effective solvent comprising one or more protic and/or aprotic solvents to form a separable mixture;
 b) combining with said separable mixture, di-p-toluoyl-L-tartaric acid;
 c) allowing a precipitate to form and collecting said solid precipitate from the mother liquid of said separable mixture, said precipitate comprising (1S,4R)-1-azabicyclo[2.2.1]heptan-3-one, di-p-toluoyl-L-tartaric acid hemisalt.

11. The process of claim 10 wherein said di-p-toluoyl-L-tartaric acid is combined with said separable mixture in an amount of from about 50% to about 100% of stoichiometry calculated as the hemisalt from the amount of (1S,4R) isomer contained in said separable mixture.

12. The process of claim 10 wherein said di-p-toluoyl-L-tartaric acid is combined with said separable mixture in an amount of from about 70% to about 90% of stoichiometry calculated as the hemisalt from the amount of (1S,4R) isomer contained in said separable mixture.

13. A process for the resolution of one (1R,4S)-1-azabicyclo[2.2.1]heptan-3-one, said process comprising:
 a) dissolving a mixture of (1R,4S)- and (1S,4R)-1-azabicyclo[2.2.1]heptan-3-one in a selective crystallization—effective solvent comprising one or more protic and/or aprotic solvents to form a separable mixture;
 b) combining with said separable mixture di-p-toluoyl-d-tartaric acid;
 c) allowing a precipitate to form and collecting said solid precipitate from the mother liquid of said separable mixture, said precipitate comprising (1R,4S)-1-azabicyclo[2.2.1]heptan-3-one, di-p-toluoyl-D-tartaric acid hemisalt.

14. The process of claim 13 wherein said di-p-toluoyl-D-tartaric acid is combined with said separable mixture in an amount of from about 50% to about 100% of stoichiometry calculated as the hemisalt from the amount of (1R,4S) isomer contained in said separable mixture.

15. The process of claim 13 wherein said di-p-toluoyl-D-tartaric acid is combined with said separable mixture in an amount of from about 70% to about 90% of stoichiometry calculated as the hemisalt from the amount of (1R,4S) isomer contained in said separable mixture.

16. A composition comprising the compound:

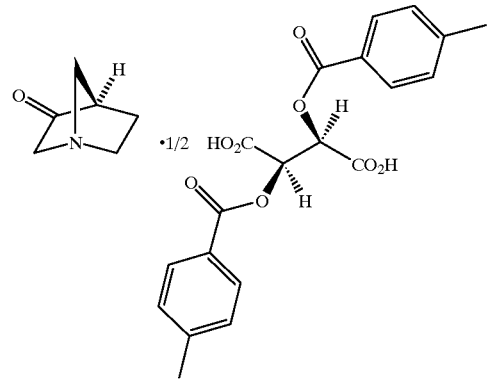

17. A composition comprising the compound:

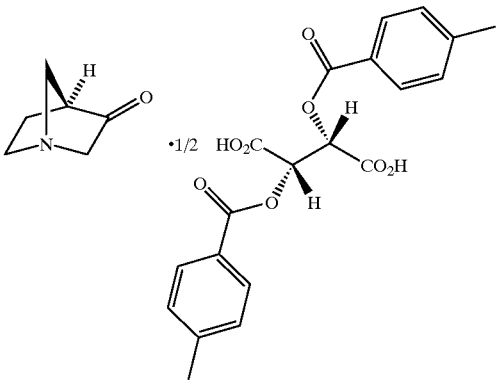

18. A composition comprising a hydrate, solvate or mixture thereof of the compound of claim 16.

19. A composition comprising a hydrate, solvate or mixture thereof of the compound of claim 17.

* * * * *

UNITED STATES PATENT AND TRADEMARK OFFICE
CERTIFICATE OF CORRECTION

PATENT NO.    : 6,121,306
DATED         : September 19, 2000
INVENTOR(S)   : Sobieray Page 1 of 1

It is certified that error appears in the above-identified patent and that said Letters Patent is hereby corrected as shown below:

Column 5,
Line 9, "nitrites" should read -- nitriles --
Line 17, "nitrites" should read -- nitriles --

Column 9,
Line 50, "1 hours" should read -- 1.5 hours --

Column 10, claim 1,
Line 56, "di-p-toluoyl-d-tartaric acid" should read -- di-p-toluoyl-D-tartaric acid --

Signed and Sealed this

Twenty-ninth Day of January, 2002

Attest:

Attesting Officer

JAMES E. ROGAN
Director of the United States Patent and Trademark Office